(12) United States Patent
Crucilla

(10) Patent No.: US 7,473,233 B2
(45) Date of Patent: Jan. 6, 2009

(54) AUTOMATED SYSTEM AND METHOD FOR DETERMINING DRUG TESTING

(75) Inventor: Chris Crucilla, Douglas, AZ (US)

(73) Assignee: Streetime Technologies, LLC, Easton, CT (US)

( * ) Notice: Subject to any disclaimer, the term of this patent is extended or adjusted under 35 U.S.C. 154(b) by 236 days.

(21) Appl. No.: 11/449,176

(22) Filed: Jun. 7, 2006

(65) Prior Publication Data

US 2006/0281978 A1 Dec. 14, 2006

Related U.S. Application Data

(60) Provisional application No. 60/688,522, filed on Jun. 7, 2005.

(51) Int. Cl.
*A61B 5/117* (2006.01)
*A61B 5/103* (2006.01)
*A61B 5/00* (2006.01)
*A61B 19/00* (2006.01)

(52) U.S. Cl. .................. 600/595; 600/300; 128/898

(58) Field of Classification Search ............... 600/544, 600/587, 595, 300; 702/119; 128/898
See application file for complete search history.

(56) References Cited

U.S. PATENT DOCUMENTS

| | | | |
|---|---|---|---|
| 6,293,150 B1 | 9/2001 | Conlan | |
| 6,351,690 B1 | 2/2002 | Lenz | |
| 6,804,661 B2 | 10/2004 | Cook | |
| 2004/0049132 A1 | 3/2004 | Barron et al. | |
| 2004/0111040 A1 | 6/2004 | Ni et al. | |
| 2005/0113650 A1 | 5/2005 | Pacione et al. | |
| 2005/0113721 A1 | 5/2005 | Reed et al. | |

OTHER PUBLICATIONS

Mini Mitter Co., Inc., Physiological and Behavioral Monitoring for Humans and Animals, Internet website pages, approximately Jun. 2005, Bend, Oregon, U.S.

*Primary Examiner*—Max Hindenburg
*Assistant Examiner*—Brian Szmal
(74) *Attorney, Agent, or Firm*—Knechtel, Demeur & Samlan

(57) ABSTRACT

An automated system and method for determining drug testing. The system enters a participant or subject into the system who is to be monitored during a probationary or other program for alcohol or drug abuse offenders. The system provides a watch for the participant to wear and record sleep pattern information of the participants through their movements and intensity of those movements. The system uploads the sleep pattern information into the computer system and conducts various tests to analyze the sleep pattern information for determining if the participant or subject has been using alcohol or other drugs and should be subjected to a confirming urinalysis exam.

20 Claims, 12 Drawing Sheets

FIG. 15

152 — TMcCall
76 — 27-Apr-2006
78 — 13:10
4
74 — 37
86 — F630448
72 — F
1126
664
605
442
1162
1126
1583
776
0
0
0
0
0
0
0
0
0
0
0
0
0
0
0
0
0
0
0
0
0
0
0
0
0
0
0
0
0
65
75
0
206
1274
220
61
0
0
206
456
534
59
0
0

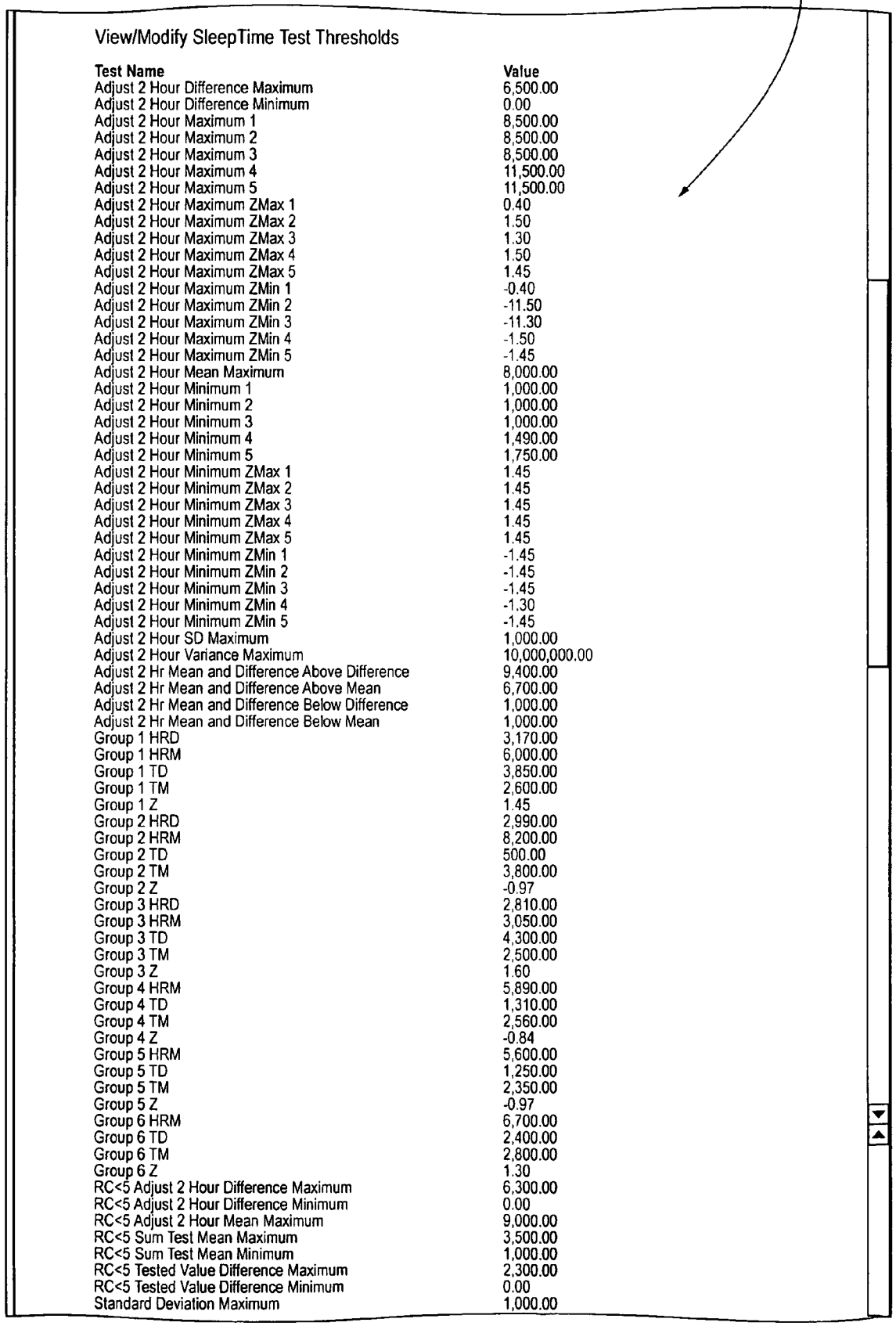

View/Modify SleepTime Test Thresholds

| Test Name | Value |
|---|---|
| Adjust 2 Hour Difference Maximum | 6,500.00 |
| Adjust 2 Hour Difference Minimum | 0.00 |
| Adjust 2 Hour Maximum 1 | 8,500.00 |
| Adjust 2 Hour Maximum 2 | 8,500.00 |
| Adjust 2 Hour Maximum 3 | 8,500.00 |
| Adjust 2 Hour Maximum 4 | 11,500.00 |
| Adjust 2 Hour Maximum 5 | 11,500.00 |
| Adjust 2 Hour Maximum ZMax 1 | 0.40 |
| Adjust 2 Hour Maximum ZMax 2 | 1.50 |
| Adjust 2 Hour Maximum ZMax 3 | 1.30 |
| Adjust 2 Hour Maximum ZMax 4 | 1.50 |
| Adjust 2 Hour Maximum ZMax 5 | 1.45 |
| Adjust 2 Hour Maximum ZMin 1 | -0.40 |
| Adjust 2 Hour Maximum ZMin 2 | -11.50 |
| Adjust 2 Hour Maximum ZMin 3 | -11.30 |
| Adjust 2 Hour Maximum ZMin 4 | -1.50 |
| Adjust 2 Hour Maximum ZMin 5 | -1.45 |
| Adjust 2 Hour Mean Maximum | 8,000.00 |
| Adjust 2 Hour Minimum 1 | 1,000.00 |
| Adjust 2 Hour Minimum 2 | 1,000.00 |
| Adjust 2 Hour Minimum 3 | 1,000.00 |
| Adjust 2 Hour Minimum 4 | 1,490.00 |
| Adjust 2 Hour Minimum 5 | 1,750.00 |
| Adjust 2 Hour Minimum ZMax 1 | 1.45 |
| Adjust 2 Hour Minimum ZMax 2 | 1.45 |
| Adjust 2 Hour Minimum ZMax 3 | 1.45 |
| Adjust 2 Hour Minimum ZMax 4 | 1.45 |
| Adjust 2 Hour Minimum ZMax 5 | 1.45 |
| Adjust 2 Hour Minimum ZMin 1 | -1.45 |
| Adjust 2 Hour Minimum ZMin 2 | -1.45 |
| Adjust 2 Hour Minimum ZMin 3 | -1.45 |
| Adjust 2 Hour Minimum ZMin 4 | -1.30 |
| Adjust 2 Hour Minimum ZMin 5 | -1.45 |
| Adjust 2 Hour SD Maximum | 1,000.00 |
| Adjust 2 Hour Variance Maximum | 10,000,000.00 |
| Adjust 2 Hr Mean and Difference Above Difference | 9,400.00 |
| Adjust 2 Hr Mean and Difference Above Mean | 6,700.00 |
| Adjust 2 Hr Mean and Difference Below Difference | 1,000.00 |
| Adjust 2 Hr Mean and Difference Below Mean | 1,000.00 |
| Group 1 HRD | 3,170.00 |
| Group 1 HRM | 6,000.00 |
| Group 1 TD | 3,850.00 |
| Group 1 TM | 2,600.00 |
| Group 1 Z | 1.45 |
| Group 2 HRD | 2,990.00 |
| Group 2 HRM | 8,200.00 |
| Group 2 TD | 500.00 |
| Group 2 TM | 3,800.00 |
| Group 2 Z | -0.97 |
| Group 3 HRD | 2,810.00 |
| Group 3 HRM | 3,050.00 |
| Group 3 TD | 4,300.00 |
| Group 3 TM | 2,500.00 |
| Group 3 Z | 1.60 |
| Group 4 HRM | 5,890.00 |
| Group 4 TD | 1,310.00 |
| Group 4 TM | 2,560.00 |
| Group 4 Z | -0.84 |
| Group 5 HRM | 5,600.00 |
| Group 5 TD | 1,250.00 |
| Group 5 TM | 2,350.00 |
| Group 5 Z | -0.97 |
| Group 6 HRM | 6,700.00 |
| Group 6 TD | 2,400.00 |
| Group 6 TM | 2,800.00 |
| Group 6 Z | 1.30 |
| RC<5 Adjust 2 Hour Difference Maximum | 6,300.00 |
| RC<5 Adjust 2 Hour Difference Minimum | 0.00 |
| RC<5 Adjust 2 Hour Mean Maximum | 9,000.00 |
| RC<5 Sum Test Mean Maximum | 3,500.00 |
| RC<5 Sum Test Mean Minimum | 1,000.00 |
| RC<5 Tested Value Difference Maximum | 2,300.00 |
| RC<5 Tested Value Difference Minimum | 0.00 |
| Standard Deviation Maximum | 1,000.00 |

FIG. 16C

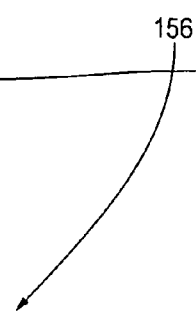

| | |
|---|---|
| Sum Mean and Difference Above Difference | 3,800.00 |
| Sum Mean and Difference Above Mean | 3,200.00 |
| Sum Mean and Difference Below Difference | 565.00 |
| Sum Mean and Difference Below Mean | 1,120.00 |
| Sum Test Maximum 1 | 1,200.00 |
| Sum Test Maximum 2 | 3,500.00 |
| Sum Test Maximum 3 | 3,900.00 |
| Sum Test Maximum 4 | 4,100.00 |
| Sum Test Maximum 5 | 5,200.00 |
| Sum Test Maximum ZMax 1 | 0.40 |
| Sum Test Maximum ZMax 2 | 1.50 |
| Sum Test Maximum ZMax 3 | 1.30 |
| Sum Test Maximum ZMax 4 | 1.50 |
| Sum Test Maximum ZMax 5 | 1.45 |
| Sum Test Maximum ZMin 1 | -0.40 |
| Sum Test Maximum ZMin 2 | -1.50 |
| Sum Test Maximum ZMin 3 | -1.30 |
| Sum Test Maximum ZMin 4 | -1.50 |
| Sum Test Maximum ZMin 5 | -1.45 |
| Sum Test Mean Maximum | 4,000.00 |
| Sum Test Mean Minimum | 0.00 |
| Sum Test Minimum 1 | 300.00 |
| Sum Test Minimum 2 | 300.00 |
| Sum Test Minimum 3 | 300.00 |
| Sum Test Minimum 4 | 1,450.00 |
| Sum Test Minimum 5 | 1,200.00 |
| Sum Test Minimum ZMax 1 | 1.45 |
| Sum Test Minimum ZMax 2 | 1.45 |
| Sum Test Minimum ZMax 3 | 1.45 |
| Sum Test Minimum ZMax 4 | 1.45 |
| Sum Test Minimum ZMax 5 | 1.45 |
| Sum Test Minimum ZMin 1 | -1.45 |
| Sum Test Minimum ZMin 2 | -1.45 |
| Sum Test Minimum ZMin 3 | -1.45 |
| Sum Test Minimum ZMin 4 | -1.30 |
| Sum Test Minimum ZMin 5 | -1.45 |
| Tested Value Difference Maximum | 5,000.0 |
| Tested Value Difference Minimum | 250.00 |
| Variance Maximum | 10,000,000.00 |
| Z and Adjusted 2 Hr Count Maximum | 7,500.00 |
| Z and Adjusted 2 Hr Count ZscoreMax | 1.60 |
| Z and Adjusted 2 Hr Count ZscoreMin | -0.80 |
| Z and Adjusted 2 Hr Difference Maximum | 6,700.00 |
| Z and Adjusted 2 Hr Difference Minimum | 0.00 |
| Z and Adjusted 2 Hr Difference ZscoreMax | 1.40 |
| Z and Adjusted 2 Hr Difference ZscoreMin | -1.50 |
| Z and Adjusted 2 Hr Mean Mean | 8,000.00 |
| Z and Adjusted 2 Hr Mean ZscoreMax | 1.40 |
| Z and Adjusted 2 Hr Mean ZscoreMin | -1.40 |
| Z and Sum During Test ZscoreMax | 1.30 |
| Z and Sum During Test ZscoreMin | -0.80 |
| Z and Test Difference Maximum | 5,000.00 |
| Z and Test Difference Minimum | 250.00 |
| Z and Test Difference ZscoreMax | 1.15 |
| Z and Test Difference ZscoreMin | -1.35 |
| Z and Test Mean Mean | 2,800.00 |
| Z and Test Mean ZscoreMax | 1.45 |
| Z and Test Mean ZscoreMin | -1.45 |
| Z and Tested Value Above Maximum | 5,200.00 |
| Z and Tested Value Above ZscoreMax | 1.40 |
| Z and Tested Value Below Minimum | 250.00 |
| Z and Tested Value Below ZscoreMin | 1.15 |
| Zscore Range 1 Maximum | 1.60 |
| Zscore Range 1 Minimum | -1.60 |
| Zscore Range 2 Maximum | 1.60 |
| Zscore Range 2 Minimum | -1.60 |
| Zscore Range 3 Maximum | 1.60 |
| Zscore Range 3 Minimum | -1.60 |

Adjust 2 Hour Difference Maximum ▼    Change

Done

AUTOMATED SYSTEM AND METHOD FOR DETERMINING DRUG TESTING

CROSS-REFERENCE TO RELATED APPLICATION

This patent application is a non-provisional application claiming priority from U.S. Provisional Application Ser. No. 60/688,522, entitled "Method and Apparatus For Determining Drug Testing" filed on Jun. 7, 2005.

FIELD OF THE INVENTION

The present invention relates to drug testing and, more particularly, to a unique automated system and method for determining, based on sleep patterns, if drug testing is necessary for individuals at risk for or recovering from drug abuse.

DESCRIPTION OF THE PRIOR ART

When individuals are arrested for driving while under the influence of alcohol, driving while inebriated, for possession and use of marijuana or other narcotic or substance, the fate of the individual rests with the court system. In almost all instances, when the individual returns to society, that individual is subjected to a probationary period. During this probationary period, the individual is required to undergo mandatory review and drug testing. As part of the mandatory review and drug testing, the individual is subjected to at least bi-weekly urinalysis exams. Each urinalysis exam consists of the individual creating a urinalysis sample while being watched by a witness such as their probation officer or other assigned personnel.

Although this system works, there are some inherent problems for the majority of individuals who comply with their probation by not taking or using illegal or prohibited drugs. First, performing the urinalysis exam while being watched by another person is invasive and humiliating for the individual and, at the very least, uncomfortable for the witness. Second, if the individual is complying with their probation, a routine bi-weekly urinalysis exam to confirm the non-use of drugs becomes costly due to all the time and expense invested in personnel required to conduct each exam and all the personnel required to analyze each exam.

To solve this problem, the Applicant has invented an automated system and method for determining if an individual is potentially still engaging in drug abuse and, therefore, should be subjected to a urinalysis exam to confirm the results and/or compliance with their probation or monitoring program. If Applicant's invention determines that the individual is not a person that should be subjected to a urinalysis exam because the individual does not appear to be engaging in drug abuse, this: (a) reduces the invasion and humiliation routinely experienced by individuals complying with their probation or monitoring program, (b) reduces the discomfort that may be experienced by the probation officer or other witness involved in the urinalysis exam, and (c) reduces the number of urinalysis exams conducted which transcends into reduced cost savings that may be expended toward other necessary matters.

Thus, there is a need and there has never been disclosed Applicant's unique automated system and method for determining drug testing.

SUMMARY OF THE INVENTION

The present invention is an automated system and method for determining drug testing. The system enters a participant or subject into the system who is to be monitored during a probationary or other program for alcohol or drug abuse offenders. The system provides a watch for the participant to wear and record sleep pattern information of the participants through their movements and intensity of those movements. The system uploads the sleep pattern information into the computer system and conducts various tests to analyze the sleep pattern information for determining if the participant or subject has been using alcohol or other drugs and should be subjected to a confirming urinalysis exam.

BRIEF DESCRIPTION OF THE DRAWINGS

The Description of the Preferred Embodiment will be better understood with reference to the following figures:

FIG. 15 is a diagram of the datafile providing the Data to be used in the various tests to conduct the analysis for determining drug testing.

FIG. 16b is a continuation of the diagram of the criteria used in the various tests to conduct the analysis for determining drug testing.

FIG. 16c is a continuation of the diagram of the criteria used in the various tests to conduct the analysis for determining drug testing.

DETAILED DESCRIPTION OF THE PREFERRED EMBODIMENT

The individuals participating in this drug abuse monitoring system through a probationary period or other agency program are referred to herein as participants. Applicant's invention is used, during this period, to detect if the participant has engaged in recent episodes of alcohol or other drug abuse. The invention analyzes the sleep patterns of the participants to determine if the sleep patterns are consistent with alcohol or other drug abuse and, if so, provides the results to the participant and/or agency requesting that the participant complete a urine toxicology test for confirming evidence of consumption of alcohol or other drugs.

Applicant's invention consists of the interaction between hardware and software. The hardware consists of a watch 20, as illustrated in FIG. 1; a reader 22, as illustrated in FIGS. 2a and 2b, and a computer system 24, as illustrated in FIGS. 2b-19.

Figure 1:
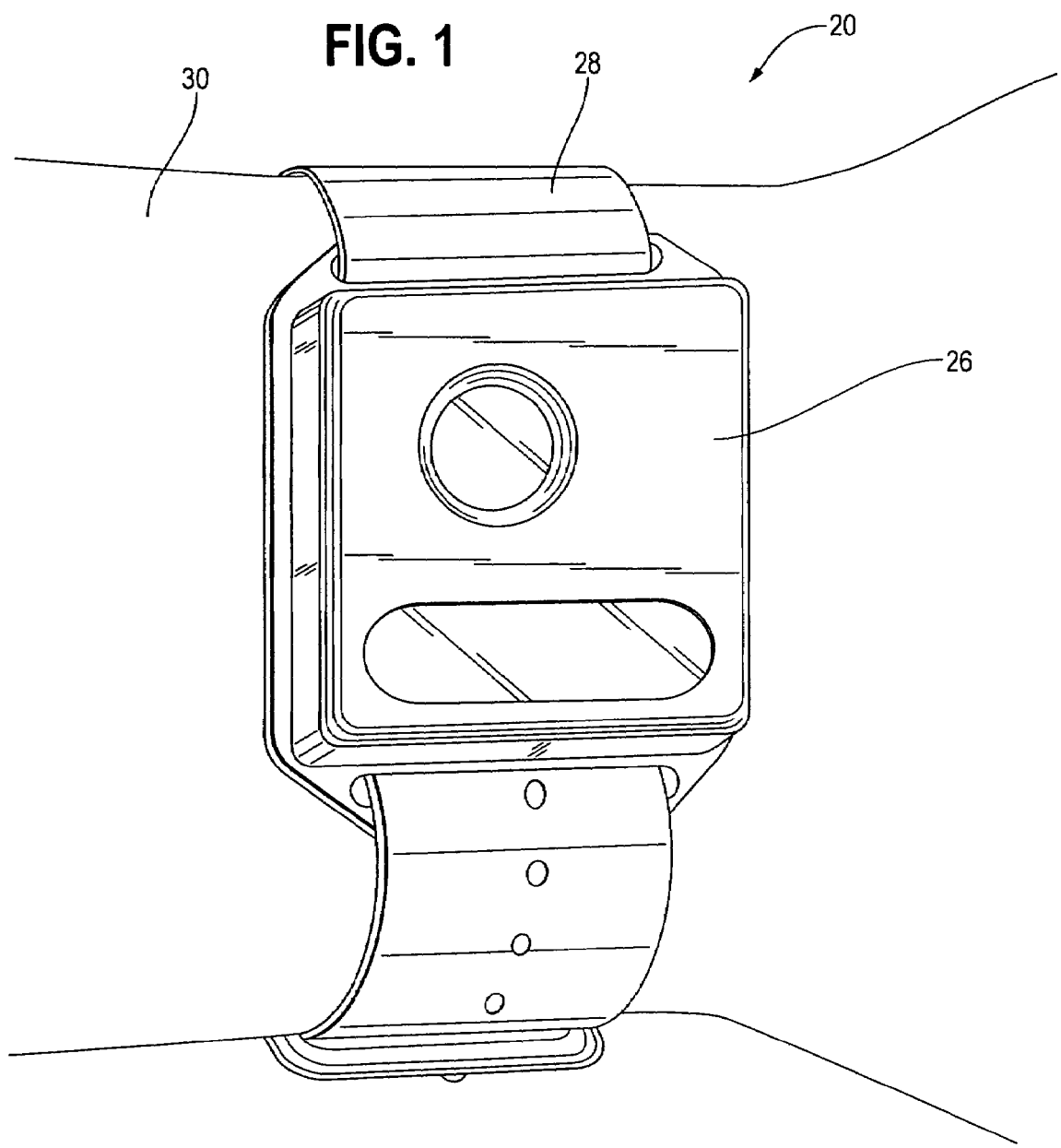
FIG. 1 is a perspective view of a watch as worn by a participant that is used in Applicant's system.
Figure 2A:
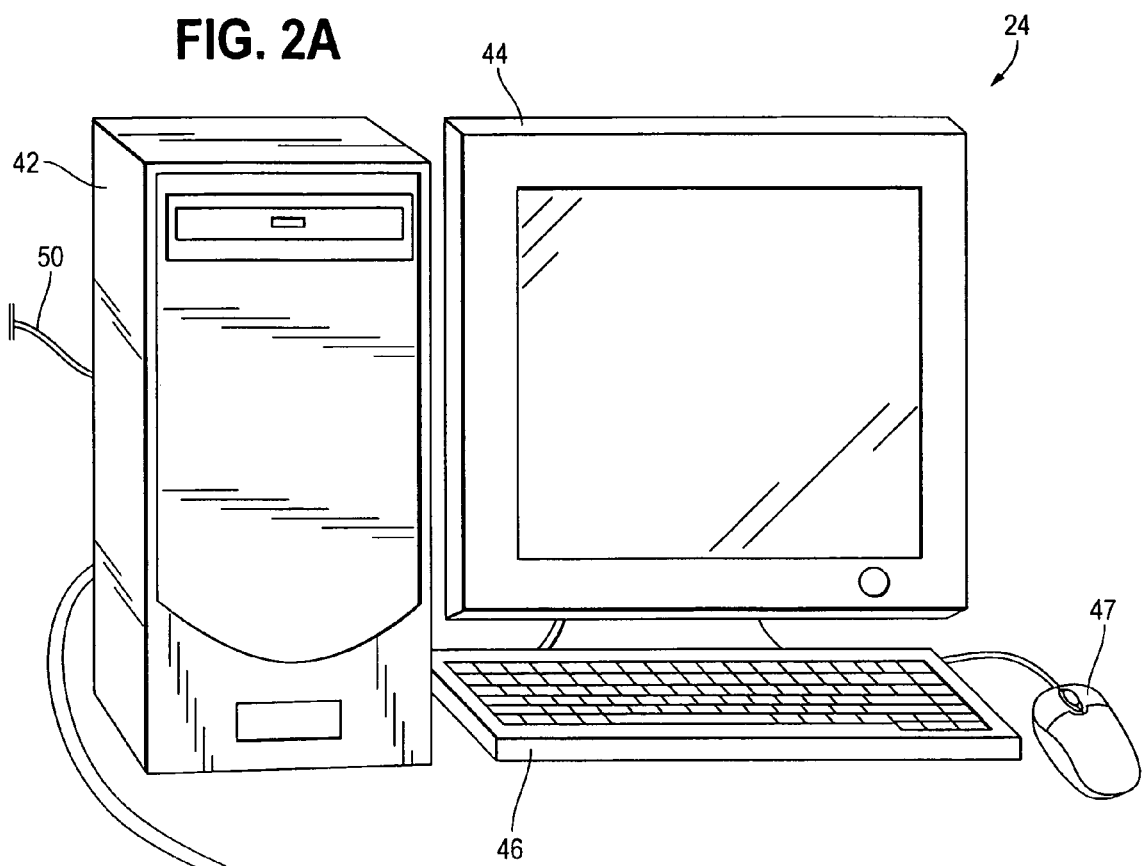
FIG. 2a is a diagram illustrating the computer hardware used in Applicant's system and, in particular, illustrating a reader and computer system.
Figure 2B:
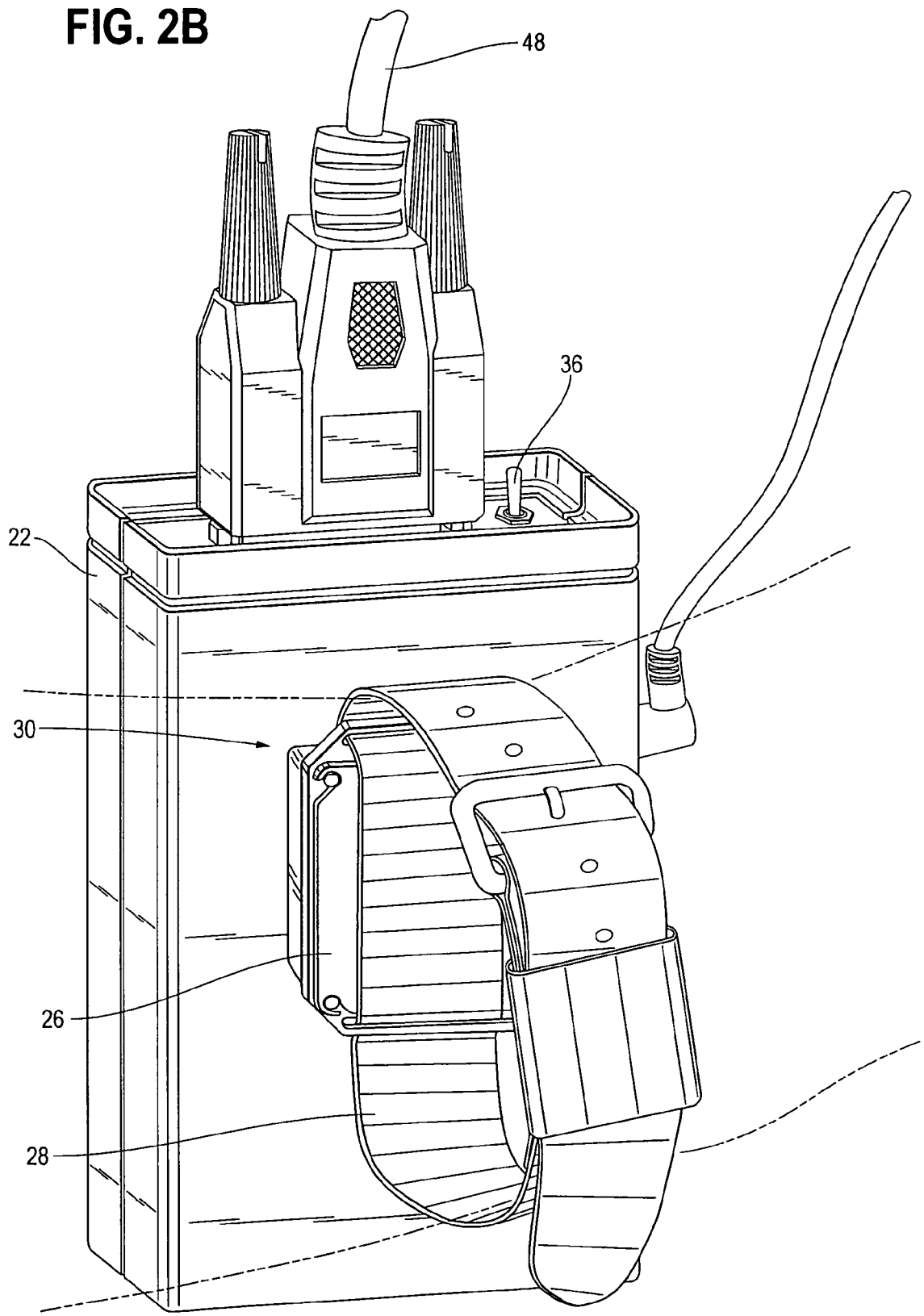
FIG. 2b is a diagram illustrating the computer hardware used in Applicant's system and, in particular, illustrating the mating of the watch to the reader.

Referring to FIG. 1, the watch 20 comprises a housing 26 attached to a band 28 or other suitable means for securing the watch 20 to a wrist 30 of a participant. The housing 26 is equipped with a highly sensitive accelerometer for recording the smallest of movements of the participant along with the intensity of such movements and the time that the movements occurred (i.e., collectively this information is referred to as "Data"). In the preferred embodiment, each movement and intensity of the participant are recorded in a whole number from zero to hundreds or thousands. Zero indicates that the participant is not moving. From there, the higher the number the greater the participant's movement and the intensity of that movement. The Data is preferably recorded in one (1) minute intervals over any period of time such as days, weeks, or months.

The watch 20 is preferably secured to the non-dominant wrist 30 of the participant. Alternatively, should the wearing of the watch 20 be forbidden or discouraged, the watch 20 may be attached to other portions of the participant's body such as their ankle. For example, this may occur when the participant is operating a jack hammer, employed in a medical setting where hygienic requirements forbid wearing watches, etc . . . Also, if the participant requests the watch 20 be worn on their ankle, it is important to determine if the participant suffers from a nervous leg syndrome, in which case, another alternative must be considered. Factors relevant to nervous leg syndrome are whether the participant commonly kicks off bed covers during the night or if a bed partner complains of kicking.

In the preferred embodiment, the watch 20 is an Actiwatch® manufactured by the Mini-Mitter Co., Inc. company located in Bend, Oreg. Alternatively, any other watch 20 may be used provided that it measures the various sleep quality data as described herein.

Referring to FIG. 2a, the reader 22 interfaces between the watch 20 and the computer system 24 to transfer the Data from the watch 20 to the computer system 24. The reader 22 comprises a faceplate 32, an alignment light display 34, on on/off switch 36 (FIG. 2b), and a power light display 38.

The on/off switch 36 is used to toggle the reader 22 between the "on" and "off" positions. When in the "on" position, a power source 40 will generate a flow of electricity to energize the reader 22 for use. Preferably, the power source 40 to generate this flow of electricity is an AC adapter or a battery. Alternatively, reader 22 may be powered by any other type of power source or means that is known to one skilled in the art. When the reader 22 is energized, the power light display 38 will engage and display a color, such as red, to visually indicate that the reader 22 is energized by the power source 40 and ready for use.

The faceplate 32 is used to communicate with the watch 20 through a short range telemetric link that is contained within the reader 22. It is this link that facilitates the transfer of the Data from the watch 20 through the reader 22 and into the computer system 24. In order for this communication to be effective, the watch 20 must be properly positioned within the faceplate 32.

The alignment light display 34 is used to engage and display a color, such as green, to indicate when the watch 20 is properly mated to the reader 22 and ready for the transfer or upload of Data to occur from the watch 20 to the computer system 24. Alternatively, the mating of the watch 20 may be accomplished while the watch 20 remains attached to the wrist 30 of the participant, as illustrated in FIG. 2b.

In the preferred embodiment, the reader 22 is an ActiReader manufactured by the Mini-Mitter Co., Inc. company located in Bend, Oreg. Alternatively, any other reader 22 may be used provided that it accurately transfers or uploads the Data from the watch 20 to the computer system 24 as described herein.

The computer system 24 consists of computer hardware and computer software. The computer hardware comprises a central processing unit 42, a computer screen 44, a keyboard 46, and a mouse 47. As computers and their components are well known in the art, it is contemplated that any computer hardware, compatible type, version, or size made by any manufacturer is acceptable as the computer system 24 to accomplish the intended purposes of Applicant's invention.

Preferably, to install and run the computer software on this computer system 24, the computer system 24 should provide at least Microsoft Windows 2000 or XP with the most recently available service pack installed, a nine (9) pin serial port or, alternatively, a USB port (not illustrated) for connecting the computer system 24 to the reader 22 by a serial or USB cable 48, a high speed internet connection 50. Additionally, if the computer system 24 is running a firewall, the firewall must be configured to allow the computer software to make TCP (outbound) calls on port 80.

Figure 3:
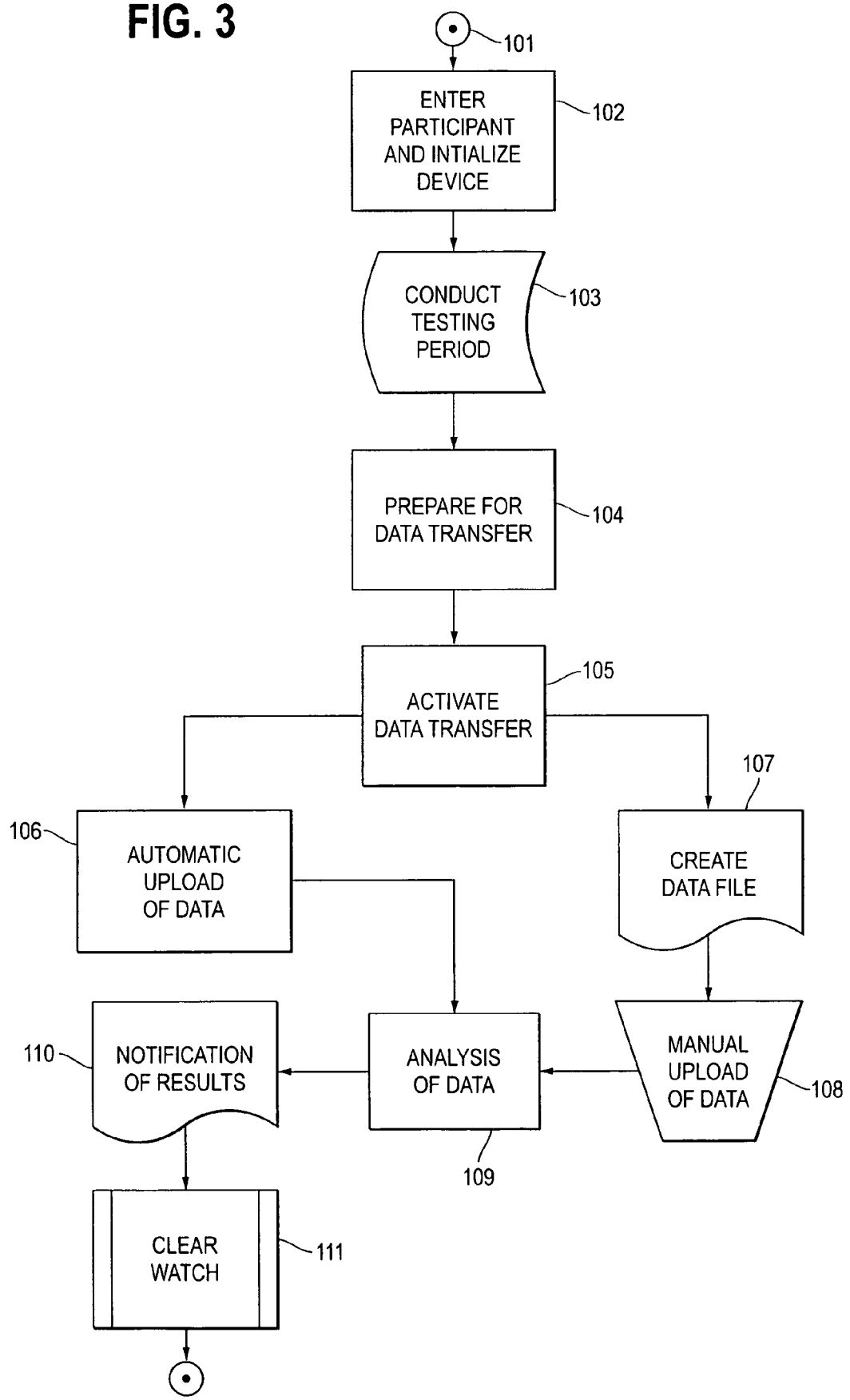
FIG. 3 is a flowchart illustrating the basic operation of Applicant's computer system for determining drug testing.

Referring to FIG. 3, there is illustrated a schematic diagram of the basic operation of Applicant's unique automated system and method for determining drug testing.

In Step 101, the process begins. If the participant (also referred to as subject) is not entered into the computer system 24, proceed to Step 102. If the participant is already entered into the computer system 24, proceed to Step 103.

Figure 4:
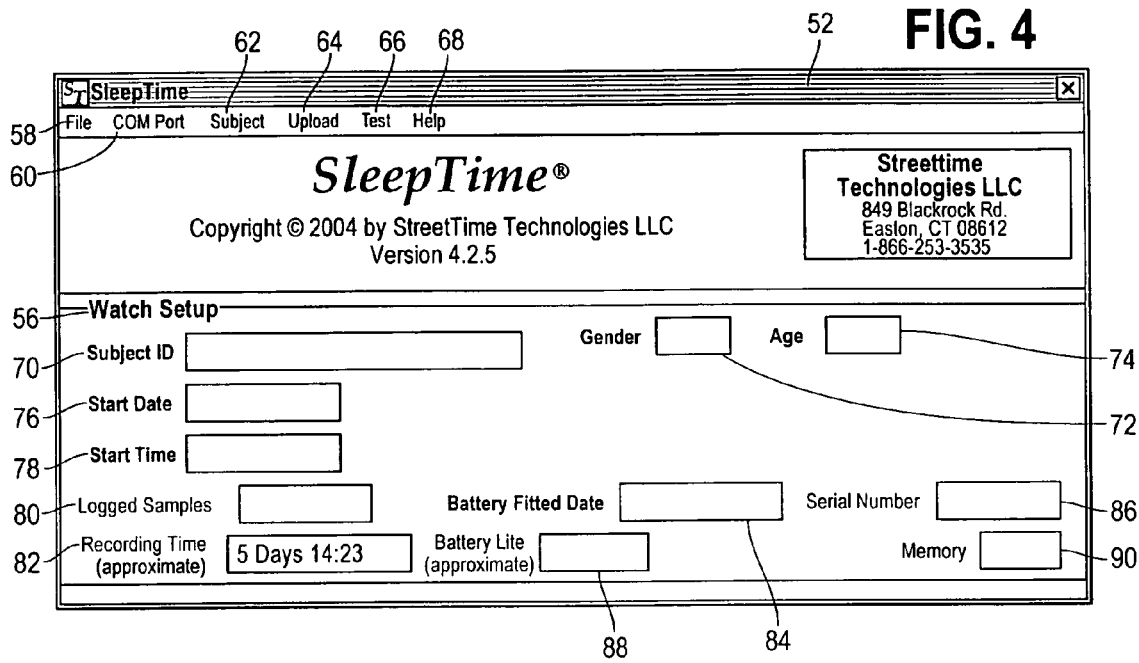
FIG. 4 is a diagram of the main interface screen of the computer software.

In Step 102, the configuration of the participant or subject is entered into the system. The computer software of the computer system 24 provides a main interface screen 52, as illustrated in FIG. 4. The main interface screen 52 comprises a menu bar 54 which provides access to all of the options of the main interface screen 52 and a setup pane 56.

The menu bar 54 provides a file heading 58, a COM port heading 60, a subject heading 62, an upload heading 64, a test heading 66, and a help heading 68. The setup pane 56 provides a subject id box 70, a gender box 72, an age box 74, a start date box 76, a start time box 78, a logged samples box 80, a recording time box 82, a battery fitted date box 84, a serial number box 86, a battery life box 88, and a memory box 90.

Figure 5:
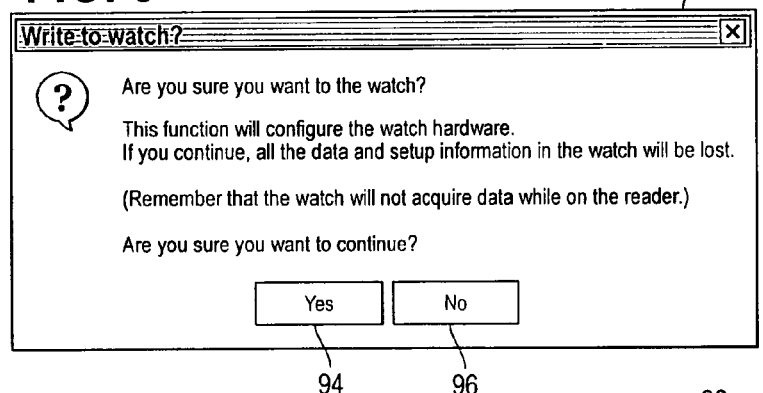
FIG. 5 is a diagram of the continue message box resulting from the selection of the subject heading from the menu bar of the main interface screen.

Using the menu bar 54, the subject heading 62 is selected which displays a continue message box 92, as illustrated in FIG. 5. The continue message box 92 displays the message "Are you sure you want to write to the watch? This function will configure the watch hardware. If you continue, all the data and setup information in the watch will be lost. (Remember that the watch will not acquire data while on the reader.) Are you sure you want to continue?" The continue message box 92 provides a yes button 94 and a no button 96. Selecting the no button 96 will stop Step 102 and the participant or subject will not be entered into the computer system 24. Selecting the yes button 94, the process of entering the participant or subject into the computer system in Step 102 continues with FIG. 6.

Figure 6:
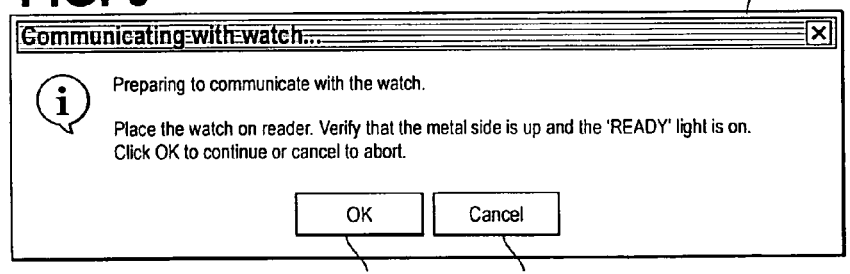
FIG. 6 is a diagram of the communicating message box resulting from the continue message box.

In FIG. 6, a communicating message box 98 is illustrated. The communicating message box 98 displays the message "Preparing to communicate with watch. Place the watch on reader. Verify that the metal side is up and the 'READY' light is on. Click OK to continue or cancel to abort." The communicating message box 98 provides an ok button 100 and a cancel button 102.

As previously discussed, to begin to prepare the watch 20 to communicate with the reader 22, the on/off switch 36 on the reader 22 is toggled to the "on" position. The reader 22 then confirms that it is ready for use when the power light display 38 is activated. The watch 20 is then mated to the reader 22 by properly positioning the watch 20 within the faceplate 32 of the reader 22. The reader 22 then confirms that the watch 20 is properly mated to the reader 22 when the alignment light display 34 is activated. If all indications that the watch 20 and the reader 22 are ready to communicate with one another, selecting the ok button 100 will continue with Step 102 and proceed to FIG. 7.

Figure 11:
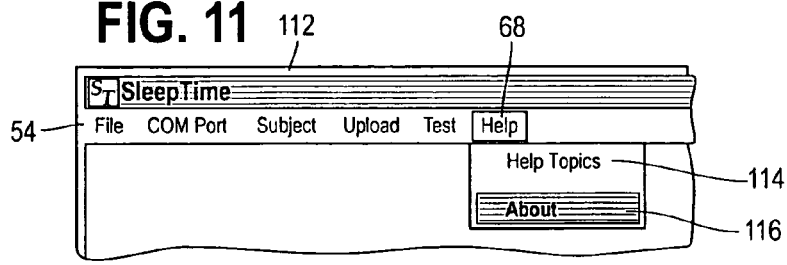
FIG. 11 is a diagram of the help drop down menu from the help heading from the menu bar of the main interface screen.

If the reader 22 does not confirm that it is ready or that the watch 20 is not properly mated to the reader 22, select the cancel button 102 to abort or stop Step 102 and proceed back to the main interface screen 52. Using the menu bar 54, selecting the help heading 68 displays a help drop down menu 112, as illustrated in FIG. 11. The help drop down menu 112 provides a help topics option 114 and an about option 116. Selecting the help topics option 114 and proceeding with the topics provided should resolve the problems encountered which are preventing the watch 20 and reader 22 from being ready to communicate with one another. This help process may be designated by the nomenclature of "Help>Help Topics". The "Help" refers to the help heading 68 and the "Help Topics" refers to the help topics option 114. When the watch 20 and the reader 22 are ready to communicate with one another, continue with Step 102 and proceed to FIG. 7.

Figure 7:
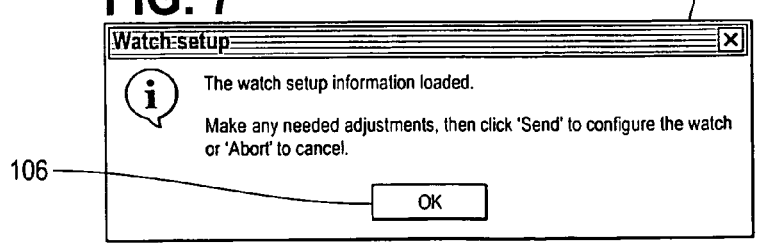
FIG. 7 is a diagram of the setup message box resulting from the communicating message box.

In FIG. 7, a setup message box 104 is illustrated. The setup message box 104 displays the message "Watch setup. The watch setup information loaded. Make any needed adjustments, then click 'Send' to configure the watch or 'Abort' to cancel." The setup message box 104 provides an ok button 106. Selecting the ok button 106, the system loads certain setup information for the participant and proceeds back to the main interface screen 52, as illustrated in FIG. 8.

Figure 8:
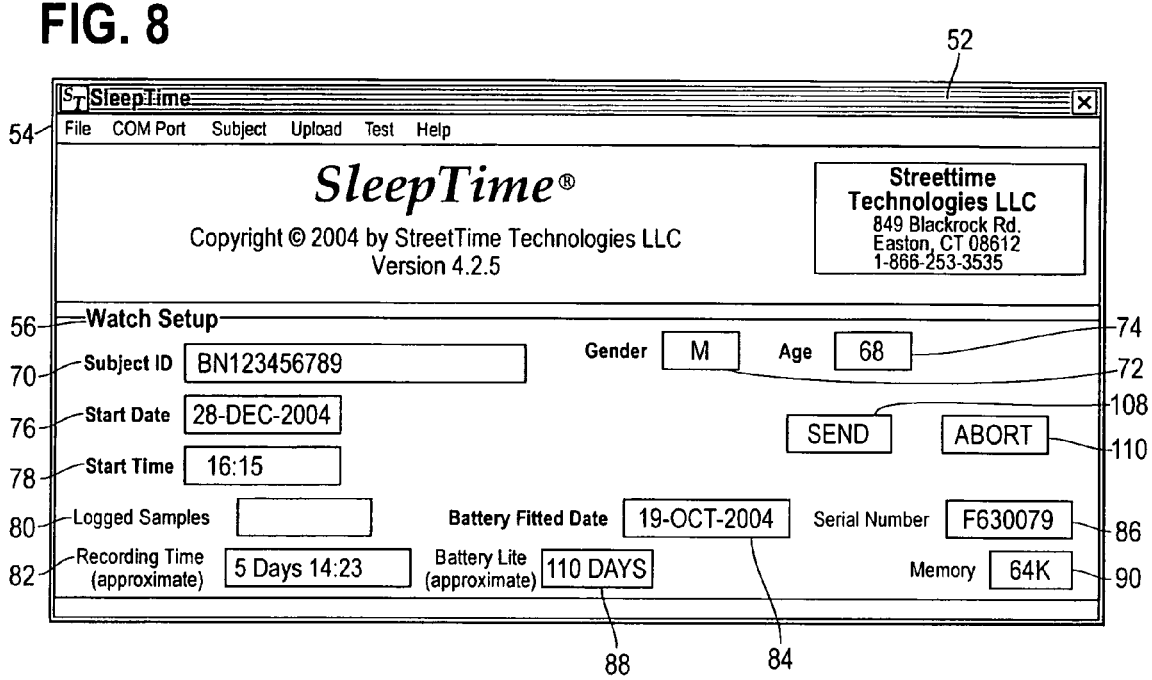
FIG. 8 is a diagram of the main interface screen of the computer software and, in particular, illustrating the loaded information of the participant or subject.

In FIG. 8, the setup pane 56 of the main interface screen 52 displays the setup information that was loaded for the participant or subject. In the non-limiting example provided, the subject id box 70 displays "BN123456789". This represents a unique numerical identifier for the participant or subject. In the preferred embodiment, the first letter is the first initial of the particpant's first name; the second letter is the first initial of the participant's last name; the remaining numeral digits are random numbers assigned to complete the subject identifier. The start date box 76 displays "28-Dec-2004" and the start time box 78 displays "16:15" indicating when the participant or subject entered the computer system 24. The setup information for the battery fitted date box 84, the battery life box 88, the serial number box 86, and the memory box 90 are likewise automatically loaded.

The participant then enters their gender in the gender box 72 which, in this example, displays an "M" indicating that the sex of the participant is a male; the age of the participant which, in this example, displays "68" indicating that the age of the participant is sixty-eight (68) years old.

The main interface screen 52 now provides a send button 108 and an abort button 110. If the information loaded into the setup pane 56 is correct, selecting the send button 108 will continue with Step 102 and proceed to FIG. 9. If, for some reason it is desired to not enter the participant or subject into the computer system 24 at this time, selecting the abort button 110 will stop Step 102.

Figure 9:
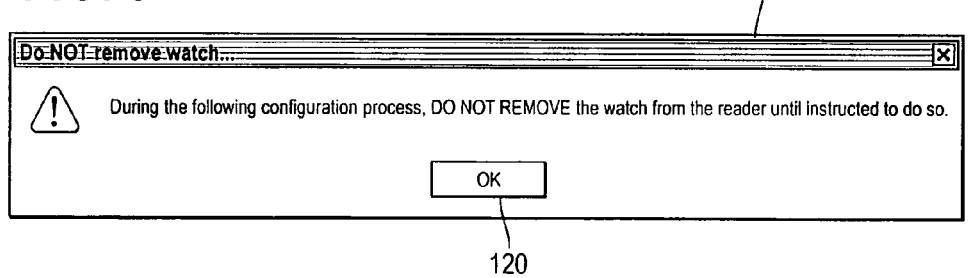
FIG. 9 is a diagram of the instruction message box resulting from confirming the loaded information of the participant or subject from the main interface screen.

In FIG. 9, an instruction message box 118 is illustrated. The instruction message box 118 displays the message "Do NOT remove watch . . . During the following configuration process, DO NOT REMOVE the watch from the reader until instructed to do so." The instruction message box 118 also provides an ok button 120. Selecting the ok button 120 confirms the instruction and compliance that the watch 20 is not to be removed from the reader 22 to allow all the loaded information to be entered. Step 102 continues and proceeds to FIG. 10.

Figure 10:
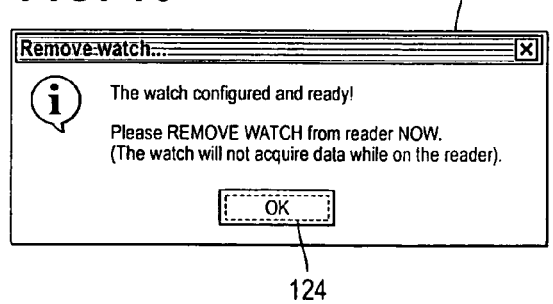
FIG. 10 is a diagram of the completion message box resulting from the instruction message box.

In FIG. 10, a completion message box 122 is illustrated. The completion message box 122 displays the message "Remove watch . . . watch configured and ready! Please REMOVE WATCH from reader NOW. (The watch will not acquire data while on the reader)." The completion message box 122 also provides an ok button 124. The participant now removes the watch 20 from the reader 22 and, if not wearing the watch 20, the participant immediately begins wearing the watch 20. Selecting the ok button 124 confirms compliance and the watch 20 begins to record Data for the testing period.

Figure 12:
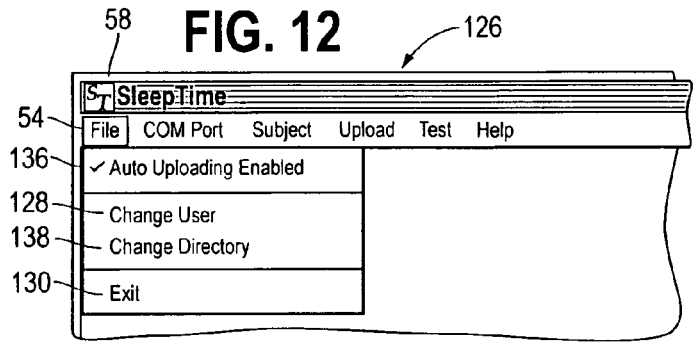
FIG. 12 is a diagram of the file drop down menu from the file heading from the menu bar of the main interface screen.

As Step 102 is completed, the process proceeds back to the main interface screen 52, as illustrated in FIG. 4. Using the menu bar 54, selecting the file heading 58 displays a file heading drop down menu 126, as illustrated in FIG. 12. The file heading drop down menu 126 provides a change user option 128, an auto uploading enabled option 136, a change directory option 138, and an exit option 130. Selecting the exit option 130 exits the computer system 24 and the Testing Period begins. This exit process may be designated by the nomenclature of "File>Exit". The "File" refers to the file heading 58 and the "Exit" refers to the exit option 130.

Alternatively, it is contemplated that the process of entering or customizing the settings of the participant or subject in Step 102 may be loaded using a toolbar icon (not illustrated) which provides an icon to select to accomplish this same step.

Once all the settings of the participant or subject have been entered or customized and Step 102 is completed and the desired Testing Period is completed, proceed to Step 103.

In Step 103 and referring back to FIG. 3, the testing period is conducted. The participant begins wearing the watch 20, as illustrated in FIG. 1. The watch 20, as previously discussed, continuously collects or records the Data in one (1) minute intervals over any period of time such as days, weeks, or months (i.e., "Testing Period"). The reason for the Testing Period is that, for example, the window of detection for EtG is eighty (80) hours once the alcohol has left the participant's body. As a result, if the Testing Period was longer than this time period, the participant may have used drugs during that time and avoided detection due to the prolonged Testing Period. When the Testing Period is completed, proceed to Step 104.

In Step 104, the transfer of the Data collected or recorded during the Testing Period is configured for transfer to the computer system 24. As previously discussed, the reader 22 is activated and then the watch 20 is properly mated to the reader 22 for facilitating the communication between them to transfer the Data to the computer system 24. When this is completed, proceed to Step 105.

In Step 105, the Data from the watch 20 is transferred through the reader 22 and uploaded into the computer system 24. If the transfer of the Data is to be automatic, proceed to Step 106. If the transfer of the data is to be done manually, proceed to Step 107.

In Step 106, if the automatic upload of the Data is desired, before the automatic upload can occur, the participant must select this option by proceeding to the main interface screen 52, as illustrated in FIG. 4. Using the menu bar 54, selecting the file heading 58 displays the file heading drop down menu 126, as illustrated in FIG. 12. Selecting the auto uploading enabled option 136 enables the Data is to be automatically uploaded into the computer system 24. This auto upload enabled process may be designated by the nomenclature of "File>Auto Uploading Enabled". The "File" refers to the file heading 58 and the "Auto Uploading Enables" refers to the auto uploading enabled option 136. In the automatic upload mode, once the auto uploading is enabled, depressing the scroll lock button on the keyboard 46 commences the automatic transfer of the Data from the watch 20 through the reader 22 and into the computer system 24. Step 106 then proceeds to the communications message box 98, as illustrated in FIG. 6.

As previously discussed, the communicating message box 98 displays the message "Preparing to communicate with watch. Place the watch on reader. Verify that the metal side is up and the 'READY' light is on. Click OK to continue or cancel to abort" and the ok button 100 and the cancel button 102. Following the same process as previously disclosed, the watch 20 and the reader 22 are to be prepared to communicate with one another. When completed, selecting the ok button 100 will proceed to FIG. 13.

Figure 13:
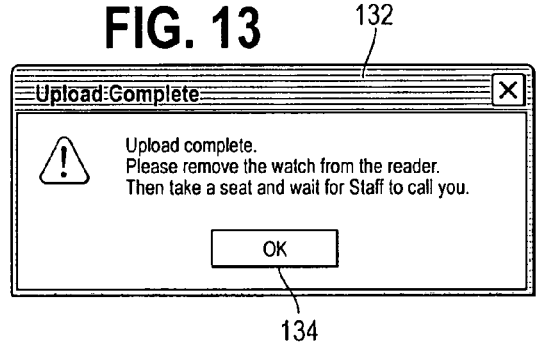
FIG. 13 is a diagram of the upload complete message box resulting from the upload of Data from the watch to the computer system.

In FIG. 13, an upload complete message box 132 is illustrated. The upload complete message box 132 displays the message "Upload Complete. Please remove the watch from the reader. Then take a seat and wait for Staff to call you." The upload complete message box 132 also provides an ok button 134. Selecting the ok button 134 acknowledges that the upload of Data from the watch 20 to the computer system 24 is completed and the process proceeds to Step 109.

Figure 14:
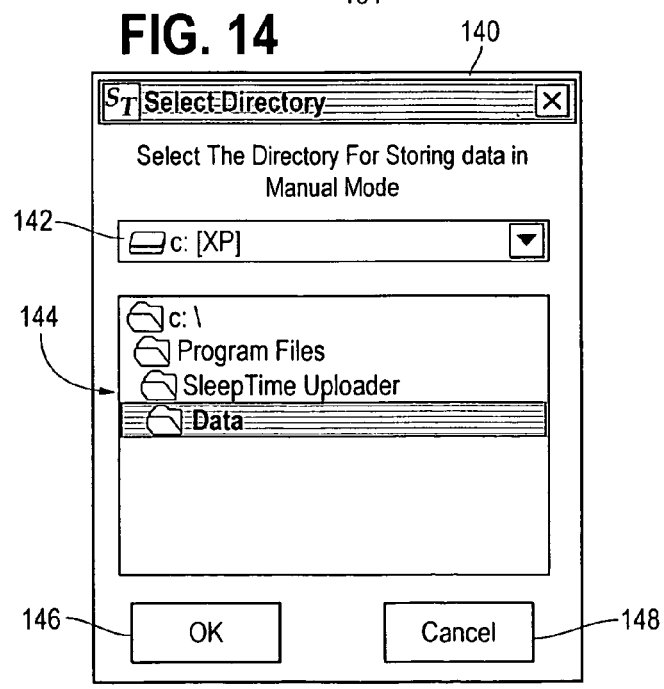
FIG. 14 is a diagram of the select directory message box resulting from the change directory option from the file heading drop down menu of the file heading from the menu bar of the main interface screen.

In Step 107, if the manual upload of the Data is desired, proceed to the main interface screen 52, as illustrated in FIG. 4. Using the menu bar 54, selecting the file heading 58 displays the file heading drop down menu 126, as illustrated in FIG. 12. Selecting the change directory option 138 displays the select directory message box 140, as illustrated in FIG. 14. In FIG. 14, the select directory message box 140 provides a computer location 142 and a computer file directory 144. Choosing the desired computer location 142 and computer file directory 144, selects where the Data uploaded into the computer system 24 is to be transferred and saved. The select directory message box 140 also provides an ok button 146 and a cancel button 148. Selecting the ok button 146 confirms the computer location 142 and computer file directory 144 selected. This directory selection process may be designated by the nomenclature of "File>Change Directory". The "File" refers to the file heading 58 and the "Change Directory" refers to the change directory option 138. In the manual mode, once the directory is selected, the Data from the watch 20 is uploaded into the computer system 24 and saved in the selected directory.

In the preferred embodiment, the data is saved in a data file 150 as a text file, as illustrated in FIG. 15. The data file 150 provides in a single row starting with the loaded participant information from the setup pane 56 in the main interface screen 52 which includes but is not limited to a participant name 152, the start date from the start date box 76, the start time from the start time box 78, the age of the participant from the age box 74, the serial number of the watch 20 from the serial number box 86, and the gender of the participant from the gender box 72. Each remaining whole numeric number 154 represents a recorded movement and corresponding intensity along with that movement ("Value"). Each recorded numeric Value is in sequential, chronological order with each recording occurring in approximately one (1) minute intervals over the Testing Period. When the Data is saved in the data file 150, the process proceeds to Step 108.

In Step 108, proceed to the main interface screen 52, as illustrated in FIG. 4. Using the menu bar 54, selecting the upload heading 64 proceeds to the communications message box 98, as illustrated in FIG. 6.

As previously discussed, the communicating message box 98 displays the message "Preparing to communicate with watch. Place the watch on reader. Verify that the metal side is up and the 'READY' light is on. Click OK to continue or cancel to abort" and the ok button 100 and the cancel button 102. Following the same process as previously disclosed, the watch 20 and the reader 22 are to be prepared to communicate with one another. When completed, selecting the ok button 100 will proceed to FIG. 13.

As previously discussed, the upload complete message box 132 displays the message "Upload Complete. Please remove the watch from the reader. Then take a seat and wait for Staff to call you" and the ok button 134. Following the same process as previously disclosed, selecting the ok button 134 acknowledges that the upload of Data from the watch 20 to the computer system 24 is completed and the process proceeds to Step 109.

Figure 16A:
FIG. 16a is a diagram of the criteria used in the various tests to conduct the analysis for determining drug testing.
Figure 17:
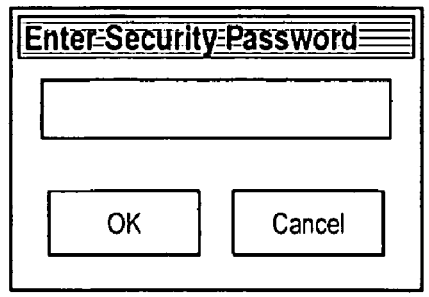
FIG. 17 is a diagram of the security password message box for entering the password of the participant to enter the system.
Figure 18:
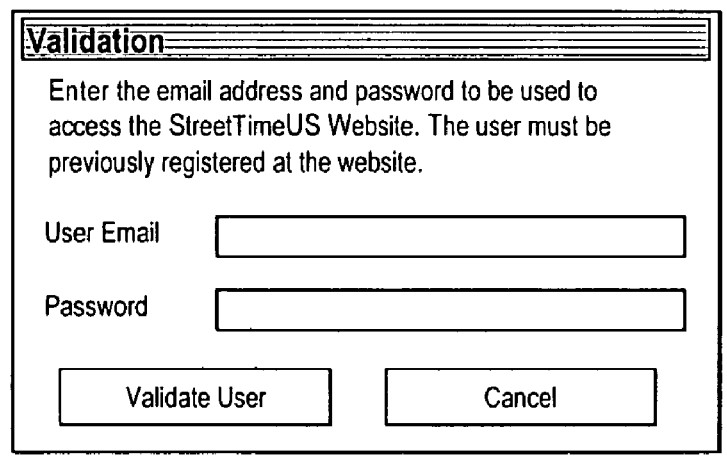
FIG. 18 is a diagram of the validation message box for validating the participant entering the system.
Figure 19:
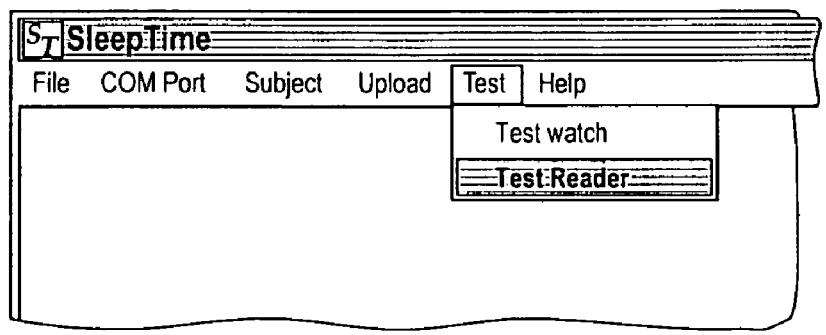
FIG. 19 is a diagram of the test drop down menu from the test heading from the menu bar of the main interface screen.

In Step 109, the Data is analyzed using various criteria 156 and tests to determine which individuals should be subjected to a urinalysis exam. The criteria 156 is provided for as illustrated in FIGS. 16(*a-c*) and is described in more detail below. The tests fall into one of three categories: (1) the preprocessing analysis tests, (2) the daily analysis tests, and (3) the combined daily analysis tests.

Each of these tests uses various terms and/or benchmarks, the definitions of which are provided below.

Sleep Threshold—A Value for a minute that is the maximum single Value allowed for the subject to be considered asleep. Currently the Sleep Threshold is where the Value is 40 or less.

Wake Period—Any minute with a Value that is greater than the Sleep Threshold, the subject is probably awake.

Contiguous Sleep—A count of the number of minutes with Values that are all less then or equal to Sleep Threshold that must be found before the subject is considered to be asleep. The time the subject fell asleep is considered to be the last minute of this interval. The default number of minutes for Contiguous Sleep is 20.

Sleep Start—This is the last minute of the Contiguous Sleep period.

Sleep Intervals—After sleep start is found, the search for sleep end is conducted by looking at readings in groups of this size. The default value is 20.

Awake Count—The number of readings in a Sleep Interval that must be Wake Periods (e.g., are above the Sleep Threshold value) before the period is considered to indicate Sleep End. The default Value is 10.

Sleep End—Beginning with Sleep Start readings are looked at in groups of discrete Sleep Intervals. If the number of readings that are above the Sleep Threshold in a Sleep Interval is greater than the Awake Count then Sleep End is found. The Sleep End time is the last minute in the Sleep Interval that is triggered by Sleep End. It is now appropriate to look to see if the subject is waking up.

Wake Count—The number of contiguous Wake Periods that must be found before the subject is considered to be awake. The default Wake Count is 8.

Awake Time—Beginning with Sleep End a group of Wake Count contiguous Wake Periods (Values greater than the Sleep Threshold) indicates Awake Time. The actual time of awakening is the time of the last Wake Period.

Awake Setback—This is the number of minutes subtracted from the Awake Time before Analysis begins. The default Awake Setback is 1 hour.

Analysis Interval—This is the time period between Sleep Start and Awake Time less the Await Setback that is used for the analysis. The Analysis Interval must be a minimum of two hours and may be a maximum of four hours. If the interval is less then four hours, threshold values are pro-rated.

Adjust 2 Hour Sleep—This is the minimum number of minutes that must be Wake Periods to trigger a less than 2 hour sleep condition when looking for Awake Time.

Adjust 2 Hour Sleep Count—When looking for Awake Time the number of minutes that have Values above the Sleep Threshold during sleep are tracked for each group of Wake Count intervals. This value is the maximum of those Values.

Maximum Number of Readings—Specifies the maximum number of readings to be used in summing values above the Sleep Threshold. The default Max Number of Readings is 40.

Minimum Threshold—Summed readings below this value result in Urine Analysis.

Threshold—Summed readings above this value result in Urine Analysis.

Zscore—is the difference between a Value and the mean of the Values divided by the standard deviation. The algorithms for the mean and the standard deviation are provided below.

Mean (Arithmetic Mean)

a) $\bar{x} = \frac{1}{n}\sum_{i=1}^{n} x_i = x_1 + x_2 + \ldots$

Standard Deviation a) $s = \sqrt{\frac{\sum_{i=1}^{n}(x_i - \bar{x})^2}{n-1}}$, where $\bar{x}$ is the mean of the sample.

(1) Preprocessing Analysis Tests

The analysis begins with the preprocessing analysis tests. Before the preprocessing analysis tests can be conducted, the following conditions must be met. First, the Data must cover at least four (4) continuous days for the participant. If the Data for a Testing Period is for a period of less than four days, the Data from the Testing Period can be added to the previous days of Data for the participant saved in the datafile 150 to provide the four (4) days. If the four (4) days of Data is not available, no tests are performed and Step 109 stops. Second, at the end of the Data, there must remain at least six (6) hours of Data that is excluded from the analysis. If six (6) hours of Data is not available, no tests are performed and Step 109 stops.

Once these conditions are met, the preprocessing analysis test proceeds to conduct at least the following five (5) tests.

1. The system needs to look for Contiguous Sleep at this time. If no sleep is found for twenty-four (24) hours it is an automatic fail.

2. There must be at least two (2) days of Data if the MustHave2Days flag is true. If there is not enough Data it is an automatic fail.

3. Sleep Start is fixed by the end of Contiguous Sleep. If no Sleep Start is found it is an automatic fail.

4. From Sleep Start, the system will then look for Sleep End. After Sleep End is found Awake Time is determined. The Analysis Interval can now be determined and threshold values prorated if necessary. If no Sleep Start or Awake Time can be found, or if there is less then two hours of Data, or there is a gap in the Data, the analysis terminates at this point and a urinalysis is suggested.

5. Reading Count is the sum of the largest Maximum Number of Readings Values in the Analysis Interval. A default value of 25 is used for the Maximum Number of Readings. The readings are selected if they are greater than the Sleep Threshold. If there is less than one (1) reading it is an automatic fail. The Tested Value is the sum of the data Values for the Reading Count.

All of the result values from the preprocessing tests are stored for later final processing. If there is sufficient data, then another analysis will be performed beginning twelve hours after Awake Time.

(2) Daily Analysis Tests

After all data is collected by the preprocessor. The daily analysis tests are performed for each analysis interval that produced Tested Values. Tests can be turned on or set to monitoring to obtain optimal performance. All "Z" tests are only run if there is more than one (1) Tested Value. If there is more than one Tested Value the mean, standard deviation and variance are calculated for both the Tested Values and Adjust 2 Hour Count values.

The daily analysis tests proceed to conduct at least the following eight (8) tests as applied to the criteria 156, provided in FIG. 16.

1. Sum Test Min/Max Test—For less than 2 Tested Values if the Tested Value is outside the range allowed based on the number of Reading Counts it is a fail. For multiple Tested Values if the Tested Value is outside the range allowed based on the number of Reading Counts and the Zscore is outside the associated range it is a fail.

2. Zscore Test—the zscore is tested against the 3 zscore ranges. If it is outside of all of the ranges it is a fail.

3. Z and Adjust 2 Hour Count—the zscore must be within the specified range and the Adjust 2 Hour Count must be below the specified maximum value to pass.

4. Z and Tested Value Below—if the Tested Value is less than or equal to the specified value and the zscore is less than the specified value it is a fail.

5. Z and Tested Value Above—if the Tested Value is greater than or equal to the specified value and the zscore is greater than the specified value it is a fail.

6. Adjust 2 Hour Count Test—For less than two (2) Tested Values if the Adjust 2 Hour Count is outside the range allowed based on the number of Reading Counts it is a fail. For multiple Tested Values if the Adjust 2 Hour Count is outside the range allowed based on the number of Reading Counts and the Zscore is outside the associated range it is a fail.

7. Sum During Sleep Test—this test is run if the Reading Count is less than four (4). If the sum of the Values before sleep is less than the sum of the Values during sleep it is a fail.

8. Z and Sum During Test—If the Sum Before Sleep is less than the Sum During Sleep and the Zscore is outside the specified range it is a fail.

(3) Combined Day Analysis Tests

These tests are based on means and the minimum/maximum zscore values for all tested days. All "Z" tests are only run if there is valid Zscore.

The combined day analysis tests proceeds to conduct at least the following twenty (20) tests as applied to the criteria 156, provided in FIG. 16.

1. Variance/SD Test—This test checks the Standard Deviation and Variance. If the variance of the Tested Values is greater than or equal to the Variance Maximum and the standard deviation is greater than or equal to the Standard Deviation Maximum it is a fail.

2. Adjust 2 Hour Variance/SD Test—If the variance of Adjust 2 Hour Count is greater than or equal to the Adjust 2 Hour Variance Maximum and the standard deviation is greater than or equal to the Adjust 2 Hour Standard Deviation Maximum it is a fail.

3. Adjust 2 Hour Mean Test—If the Adjust 2 Hour Mean is greater than the Adjust 2 Hour Mean Maximum it is a fail. If the number of Tested Values is less then 3 this test can not be turned to monitoring.

4. Z and Adjust 2 Hr Mean—If the minimum zscore value is below a specified Z and Adjust 2 Hr Mean ZscoreMin or the maximum zscore value is above a specified Z and Adjust 2 Hr Mean ZscoreMax and the Adjust 2 Hr Mean is greater than the Adjust 2 Hour Mean Mean it is a fail.

5. Summed Reading Mean Test—If the Tested Value Mean is less than the Sum Test Mean Minimum or the Tested Value Mean is greater than the Sum Test Mean Maximum it is a fail.

6. Z and Test Mean—If the minimum zscore value is below a specified Z and Test Mean ZscoreMin or the maximum zscore value is above a specified Z and Test Mean ZscoreMax and the Tested Value Mean is greater than the Z and Test Mean Mean it is a fail.

7. Adjust 2 Hour Count Difference Test—If the difference between the maximum Adjust 2 Hr Count and the minimum Adjust 2 Hr Count is less than the Adjust 2 Hour Difference Minimum or greater than the Adjust 2 Hour Difference Maximum it is a fail.

8. Tested Value Difference Test—If the difference between the maximum Tested Value and the minimum Tested Value is less then the Tested Value Difference Minimum or greater than the Tested Value Difference Maximum it is a fail.

9. Sum Mean and Tested Difference Below Test—If the Tested Value Mean is less than the Sum Mean and Tested Difference Below Mean and the difference between the maximum Tested Value and the minimum Tested Value is less than the Sum Mean and Tested Difference Below Difference it is a fail.

10. Sum Mean and Tested Difference Above Test—If the Tested Value Mean is greater than the Sum Mean and Tested Difference Above Mean and the difference between the maximum Tested Value and the minimum Tested Value is greater than the Sum Mean and Tested Difference Above Difference it is a fail.

11. Adjust 2 Hr Mean and Adjust 2 Hr Difference Below Test—If the Adjust 2 Hr Mean is less than the Adjust 2 Hr Mean and Difference Below Mean and the difference between the maximum Adjust 2 Hour Count and the minimum Adjust 2 Hour Count is less than the Adjust 2 Hr Mean and Difference Below Difference it is a fail.

12. Adjust 2 Hr Mean and Adjust 2 Hr Difference Above Test—If the Adjust 2 Hr Mean is greater than the Adjust 2 Hr Mean and Difference Above Mean and the difference between the maximum Adjust 2 Hour Count and the minimum Adjust 2 Hour Count is greater than the Adjust 2 Hr Mean and Difference Above Difference it is a fail.

13. Z and Adjust 2 Hour Difference Test—If the minimum zscore value is below a specified Z and Adjust 2 Hr Difference ZscoreMin or the maximum zscore value is above a specified Z and Adjust 2 Hr Difference ZscoreMax and the difference between the minimum and maximum Adjust 2 Hr Counts is less than the Z and Adjust 2 Hr Difference Minimum or greater than the Z and Adjust 2 Hr Difference Maximum it is a fail.

14. Z and Tested Value Difference Test—If the minimum zscore value is below a Z and Adjust 2 Hr Difference ZscoreMin or the maximum zscore value is above a specified Z and Adjust 2 Hr Difference ZscoreMax and the difference between the minimum and maximum Tested Values is less than the Z and Test Difference Minimum or greater than the Z and Test Difference Maximum it is a fail.

15. Group 1 Test (TM<HRM>HRD<TD>Z)—If the Tested Value Mean is less than Group 1 TM and the Adjust 2 Hour Mean is greater than Group 1 HRM and the Adjust 2 Hour Difference is less than Group 1 HRD and the Tested Value Difference is greater than Group 1 TD and the Zscore Maximum is greater than Group 1 Z it is a fail.

16. Group 2 Test (TM>HRM>HRD<TD<Z)—If the Tested Value Mean is greater than Group 2 TM and the Adjust 2 Hour Mean is greater than Group 2 HRM and the Adjust 2 Hour Difference is less than Group 2 HRD and the Tested Value Difference is less than Group 2 TD and the Zscore Minimum is less than Group 2 Z it is a fail.

17. Group 3 Test (TM<HRM<HRD<TD>Z)—If the Tested Value Mean is less than Group 3 TM and the Adjust 2 Hour Mean is less than Group 3 HRM and the Adjust 2 Hour Difference is less than Group 3 HRD and the Tested Value Difference is greater than Group 3 TD and the Zscore Maximum is greater than Group 3 Z it is a fail.

18. Group 4 Test (TM>HRM>TD<Z)—If the Tested Value Mean is greater than Group 4 TM and the Adjust 2 Hour Mean is greater than Group 4 HRM and the Tested Value Difference is less than Group 4 TD and the Zscore Minimum is less than Group 4 Z it is a fail.

19. Group 5 Test (TM<HRM<TD<Z)—If the Tested Value Mean is less than Group 5 TM and the Adjust 2 Hour Mean is less than Group 5 HRM and the Tested Value Difference is less than Group 5 TD and the Zscore Minimum is less than Group 5 it is a fail.

20. Group 6 Test (TM>HRM>TD>Z)—If the Tested Value Mean is greater than Group 6 TM and the Adjust 2 Hour Mean is greater than Group 6 HRM and the Tested Value Difference is greater than Group 6 TD and the Zscore Maximum is greater than Group 6 Z it is a fail.

Final Result Processing

If the most recent urine test requested is for more than eighty (80) hours from the date the analysis is run, a warning is added to the email to that effect. The eighty (80) hours are calculated as the date analyzed plus the Awake Time−Awake Setback−4 hours.

If all of the results from the preprocessing analysis tests, the daily analysis tests, and the combined daily tests is a pass, then all indications based upon the participant's sleep patterns is that the participant has not engaged in alcohol or other drug abuse during this Testing Period and therefore it is suggested that the participant is complying with their probationary or other program. If, however, any one of the results from the preprocessing analysis tests, the daily analysis tests, or the combined daily tests is a fail, then indications are, based upon the participant's sleep patterns, that the participant has engaged in some alcohol or other drug abuse during the Testing Period and therefore it is suggested that the participant be subjected to a urine analysis exam to confirm the results. Once this Step 109 is completed, proceed to Step 110, as illustrated in FIG. 3.

In Step 110, a notification of the results of the analysis is sent to the participant and/or the agency monitoring the participant. In the preferred embodiment, the participant and/or the agency monitoring the participant must have an active, functioning e-mail address to receive the notification of the results. The results of the analysis provide one of two outcomes, a positive outcome (i.e., Analysis completed—No alcohol or other drug indicators); or, a negative outcome (i.e., Analysis completed—urine test suggested). If a positive outcome results, all indications are the participant is free of alcohol or other drug abuse during the Testing Period and should not be subjected to a urinalysis exam. If a negative outcome results, all indications are the participant has engaged in some alcohol or other drug abuse during the Testing Period and should be subjected to a urinalysis exam to confirm the analysis. Step 110 is now completed, proceed to Step 111.

In Step 111, the Data on the watch 20 is completely cleared or erased. The watch 20 then begins to record new data for the next Testing Period and the process starts over again.

Thus, there has been provided a unique automated system and method for determining drug testing of individuals at risk for drug abuse. While the invention has been described in conjunction with a specific embodiment, it is evident that many alternatives, modifications and variations will be apparent to those skilled in the art in light of the foregoing description. Accordingly, it in intended to embrace all such alternatives, modifications and variations as fall within the spirit and scope of the invention.

What is claimed is:

1. A computer based method for determining if a participant should be tested for drugs, comprising the steps of:
   (a) placing a monitoring device on the participant to record data of the participant;
   (b) creating a predetermined set of sleep pattern criteria for the participant, each sleep pattern criteria having assigned to it a criteria value;
   (c) defining a plurality of benchmarks to apply to the data;
   (d) calculating a set of measurements from the benchmarks, each measurement having a measurement value as determined from the data;
   (e) defining a plurality of tests, each of the plurality of tests using at least one of the measurement values from the set of measurements;
   (f) applying each of the plurality of tests by comparing the measurement values from each of the plurality of tests to the sleep pattern criteria values for the participant for determining a plurality of test results corresponding to each of the plurality of tests;
   (g) analyzing each of the plurality of test results for making a final determination of the results; and
   (h) providing notification of the final determination of the results and whether the participant should be tested for drugs.

2. The method of claim 1 and further comprising the step of entering unique information about the participant in a computer for initializing the monitoring device.

3. The method of claim 1 and further comprising the step of using a watch as the monitoring device.

4. The method of claim 1 and further comprising the step of creating the data from the physical movements of the participant.

5. The method of claim 1 and further comprising the step of transferring the data from the monitoring device to the computer.

6. The method of claim 5 and further comprising the step of providing a reader, with the monitoring device communicating with the reader for transferring the data from the monitoring device through the reader and into the computer.

7. The method of claim 5 and further comprising the step of automatically transferring the data from the monitoring device to the computer.

8. The method of claim 5 and further comprising the step of manually transferring the data from the monitoring device to the computer.

9. The method of claim 1 and further comprising the step of saving the data transferred from the monitoring device to the computer, the data being saved in a datafile residing in the computer.

10. The method of claim 1 and further comprising the step of selecting the plurality of tests from the group consisting of a preprocessing analysis test, a daily analysis test, and a combined daily analysis test.

11. The method of claim 1 and further comprising the step of selecting the plurality of test results corresponding to each of the plurality of tests from the group consisting of pass and fail.

12. The method of claim 11 and further comprising the step of making the final determination of the results a pass if each of the plurality of test results is a pass.

13. The method of claim 11 and further comprising the step of making the final determination of the results a fail if any one of the plurality of test results is a fail.

14. A computer based method for determining if a participant should be tested for drugs, comprising the steps of:
   (a) placing a monitoring device on the participant to record data of the participant;
   (b) providing a reader, with the monitoring device communicating with the reader for transferring the data from the monitoring device through the reader and into the computer;
   (c) creating a predetermined set of sleep pattern criteria for the participant, each sleep pattern criteria having assigned to it a sleep pattern criteria value;
   (d) determining a plurality of sleep pattern information for the participant from the data;
   (e) assigning a set of testing values to the plurality of sleep pattern information for the participant;
   (f) defining a plurality of tests, each of the plurality of tests using at least one of the testing values;
   (g) applying each of the plurality of tests by comparing the testing values from each of the plurality of tests to the sleep pattern criteria values for the participant for determining a plurality of test results corresponding to each of the plurality of tests; and
   (h) applying the plurality of test results for making a final determination as to whether the participant should be tested for drugs.

15. The method of claim 14 and further comprising the step of analyzing each of the plurality of test results for making a final determination of the results.

16. The method of claim 15 and further comprising the step of providing notification of the final determination of the results and whether the participant should be tested for drugs.

17. The method of claim 16 and further comprising the step of selecting the plurality of test results corresponding to each of the plurality of tests from the group consisting of pass and fail.

18. The method of claim 17 and further comprising the step of making the final determination of the results a pass if each of the plurality of test results is a pass.

19. The method of claim 18 and further comprising the step of making the final determination of the results a fail if any one of the plurality of test results is a fail.

20. A computer based method for determining if a participant should be tested for drugs, comprising the steps of:
    if the participant is to be entered, then performing the following step (a):
        (a) entering the participant in a computer for initializing a monitoring device; if the participant is entered into the computer and the monitoring device is initialized, then performing the following step (b):
        (b) wearing the monitoring device to record data of the participant; starting the recording of the data of the participant; if the data is to be transferred to the computer, then performing the following steps (d)-(g):
        (d) connecting a reader to the computer;
        (e) mating the monitoring device to the reader;
        (f) confirming the successful mating of the monitoring device to the reader;
        (g) transferring the data from the monitoring device through the reader and into the computer;
    if the data is to be analyzed, then performing the following steps (h)-(k):
        (h) creating a predetermined set of sleep pattern criteria to apply to the participant, each sleep pattern criteria having assigned to it a sleep pattern criteria value;
        (i) determining a plurality of sleep pattern information for the participant from the data, each of the plurality of sleep pattern information defining a sleep pattern value;
        (j) defining a plurality of tests, each of the plurality of tests using at least one of the sleep pattern values;
        (k) applying each of the plurality of tests by comparing the sleep pattern values from each of the plurality of tests to the sleep pattern criteria values of the participant for determining a plurality of test results corresponding to each of the plurality of tests;
    If the analysis is not stopped during any of the plurality of tests, then performing the following steps (l)-(m):
        (l) analyzing each of the plurality of test results for making a final determination of the results; and
        (m) providing notification of the final determination of the results and whether the participant should be tested for drugs.

\* \* \* \* \*